(12) United States Patent
Briand et al.

(10) Patent No.: US 7,402,587 B2
(45) Date of Patent: Jul. 22, 2008

(54) CRYSTALLINE FORMS OF A PYRIDINYL-SULFONAMIDE AND THEIR USE AS ENDOTHELIN RECEPTOR ANTAGONISTS

(75) Inventors: Thierry Briand, Huningue (FR); Alexander Bilz, Bad Krozingen (DE); Fritz Blatter, Reinach (FR); Martin Szelagiewicz, Münchenstein (DE)

(73) Assignee: Speedel Pharma AG, Basel (CH)

( * ) Notice: Subject to any disclaimer, the term of this patent is extended or adjusted under 35 U.S.C. 154(b) by 0 days.

(21) Appl. No.: 11/596,260

(22) PCT Filed: May 12, 2005

(86) PCT No.: PCT/EP2005/052187

§ 371 (c)(1),
(2), (4) Date: Nov. 13, 2006

(87) PCT Pub. No.: WO2005/113543

PCT Pub. Date: Dec. 1, 2005

(65) Prior Publication Data

US 2007/0173520 A1    Jul. 26, 2007

(30) Foreign Application Priority Data

May 13, 2004    (EP) .................... 04102110

(51) Int. Cl.
*C07D 401/14*    (2006.01)
*A61K 31/506*    (2006.01)

(52) U.S. Cl. ...................... 514/269; 544/319
(58) Field of Classification Search ............... 544/319; 514/269
See application file for complete search history.

(56) References Cited

U.S. PATENT DOCUMENTS 6,417,360 B1    7/2002    Breu et al.
2002/0137933 A1    9/2002    Breu et al.

FOREIGN PATENT DOCUMENTS

WO    00/52007    9/2000

OTHER PUBLICATIONS

Simone, Oncology: Introduction, Cecil Textbook of Medicine, 20th Edition, vol. 1, pp. 1004-1010, 1996.*
Rubanyi et al., Endothelins: Molecular Biology, Biochemistry, Pharmacology, Physiology, and Pathophysiology, Pharmacologial Reviews, vol. 46, No. 3, pp. 325-415, 1994.*
Mino R. Caira, "Crystalline Polymorphism of Organic Compounds", Topics in Current Chemistry, vol. 198, pp. 163-208, XP001156954, 1998.
Sophie-Dorothée Clas, "The importance of characterizing the crystal form of the drug substance during drug development", Current Opinion in Drug Discovery and Development, vol. 6, No. 4, pp. 550-560, XP009031924, Jul. 2003.
E. Doelker, "Modifications cristallines et transformations polymorphes au cours des opérations galéniques", Annales Pharmaceutiques Francaises, vol. 60, No. 3, pp. 161-176, XP009003219, 2002.

* cited by examiner

*Primary Examiner*—Deepak Rao
(74) *Attorney, Agent, or Firm*—Wenderoth, Lind & Ponack, L.L.P.

(57) ABSTRACT

Crystalline forms A and B of 5-methyl-pyridine-2-sulfonic acid [6-methoxy-5-(2-methoxy-phenoxy)-2-pyridin-4-yl-pyrimidin-4-yl]-amide of formula (I) are described, whereby form B is the most stable form. 5-methyl-pyridine-2-sulfonic acid [6-methoxy-5-(2-methoxy-phenoxy)-2-pyridin-4-yl-pyrimidin-4-yl]-amide also forms solvates with, for example, ethanol, acetone, tetrahydrofuran, methanol, isopropanol, 2-butanone and dichloromethane.

9 Claims, 5 Drawing Sheets

CRYSTALLINE FORMS OF A PYRIDINYL-SULFONAMIDE AND THEIR USE AS ENDOTHELIN RECEPTOR ANTAGONISTS

FIELD OF THE INVENTION

The present invention relates to stable crystalline forms of 5-methyl-pyridine-2-sulfonic acid [6-methoxy-5-(2-methoxy-phenoxy)-2-pyridin-4-yl-pyrimidin-4-yl]-amide. This invention also relates to processes for preparing the stable crystalline forms of 5-methyl-pyridine-2-sulfonic acid [6-methoxy-5-(2-methoxy-phenoxy)-2-pyridin-4-yl-pyrimidin-4-yl]-amide. This invention also relates to compositions comprising 5-methyl-pyridine-2-sulfonic acid [6-methoxy-5-(2-methoxy-phenoxy)-2-pyridin-4-yl-pyrimidin-4-yl]-amide and a pharmaceutically acceptable carrier, and to methods of using 5-methyl-pyridine-2-sulfonic acid [6-methoxy-5-(2-methoxy-phenoxy)-2-pyridin-4-yl-pyrimidin-4-yl]-amide and compositions thereof for the treatment or prophylaxis of disorders which are associated with abnormal vascular tone and/or endothelial dysfunction.

BACKGROUND TO THE INVENTION 5-methyl-pyridine-2-sulfonic acid [6-methoxy-5-(2-methoxy-phenoxy)-2-pyridin-4-yl-pyrimidin-4-yl]-amide corresponding to the formula

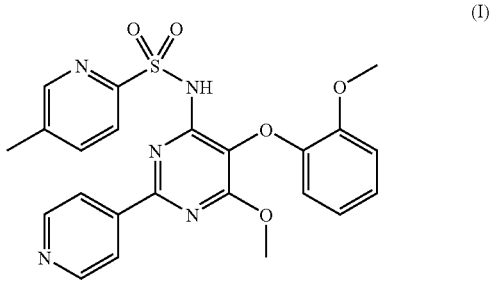

(I)

is an inhibitor of endothelin receptors. WO00/52007 describes the preparation of said compound which is crystallized from Me2Cl2.

Own investigations have shown that there exist two distinct crystalline forms, hereinafter referred to as form A and form B, as well as a number of further solvates, in particular the methanol, ethanol, isopropanol, dichloromethane, acetone, methyl ethyl ketone and tetrahydrofuran solvates.

It was further surprisingly found that the thermodynamically stable crystalline form—form B—can be prepared under controlled conditions and that said form B can be prepared with a reliable method in an industrial scale, which is easy to handle and to process in the manufacture and preparation of formulations.

SUMMARY OF THE INVENTION

This invention provides two crystalline forms A and B of 5-methyl-pyridine-2-sulfonic acid [6-methoxy-5-(2-methoxy-phenoxy)-2-pyridin-4-yl-pyrimidin-4-yl]-amide and processes for the preparation thereof. This invention further provides pseudopolymorphs (solvates) of said compound.

DETAILED DESCRIPTION OF THE INVENTION

A first object of the invention is a crystalline form of 5-methyl-pyridine-2-sulfonic acid [6-methoxy-5-(2-methoxy-phenoxy)-2-pyridin-4-yl-pyrimidin-4-yl]-amide which exhibits a characteristic X-ray powder diffraction pattern (as shown in FIG. 1), with characteristic peaks expressed in d-values (Å): 9.0 (vs), 7.8 (m), 6.2 (s), 5.48 (m), 5.30 (m), 5.07 (m), 4.67 (s), 4.52 (m), 4.23 (m), 4.14 (m) 3.79 (m), 3.57 (s), 3.42 (m), 3.23(m) and 3.02(m); hereinafter designated as form A.

Polymorph form A is a solid powder with a particle size in the range from 1 to 500 μm, preferably 5 to 300 μm, and more preferably 5 to 200 μm. The polymorph A is hygroscopic and adsorbs water to a content of about 5 percent by weight (when stored under humid conditions), which is continuously released between 50° C. and 200° C., when heated at a rate of 10° C./minute. The polymorph A is especially suitable as an intermediate and starting material to produce stable polymorph forms.

In a further embodiment, the present invention comprises a crystalline form of 5-methyl-pyridine-2-sulfonic acid [6-methoxy-5-(2-methoxy-phenoxy)-2-pyridin-4-yl-pyrimidin-4-yl]-amide, which exhibits a characteristic X-ray powder diffraction pattern (as shown in FIG. 2) with characteristic peaks expressed in d-values (Å): 10.7 (m), 9.4 (m), 8.6 (vs), 8.3 (m), 7.6 (m), 6.7 (m), 6.4 (m), 6.0 (m), 5.69 (m), 5.30 (m), 5.17 (m), 4.95 (vs), 4.76 (m), 4.56 (m), 4.43 (s), 4.13 (vs), 3.80 (s), 3.45 (s), 3.41 (s), 3.37 (s) and 3.03 (m) hereinafter designated as form B.

Polymorph B is a stable compound with a suitable morphology, which can be easily processed and handled due to its stability, possibility for preparation by targeted conditions, its suitable morphology and particle size. These outstanding properties render polymorph form B especially suitable for pharmaceutical application. Yet a further advantage of form B is that it may easily be produced essentially free of any residual solvents under very moderate drying conditions.

Here and in the following, the abbreviations used for the peak intensities of the diffraction pattern mean: (vvs)=very very strong intensity; (vs)=very strong intensity; (s)=strong intensity; (m)=medium intensity; (w)=weak intensity and (vw)=very weak intensity.

In still another preferred embodiment, the present invention comprises a crystalline form A of 5-methyl-pyridine-2-sulfonic acid [6-methoxy-5-(2-methoxy-phenoxy)-2-pyridin-4-yl-pyrimidin-4-yl]-amide, which exhibits characteristic X-ray powder diffraction patterns as exhibited in FIG. 1.

In still another preferred embodiment, the present invention comprises a crystalline form B of 5-methyl-pyridine-2-sulfonic acid [6-methoxy-5-(2-methoxy-phenoxy)-2-pyridin-4-yl-pyrimidin-4-yl]-amide, which exhibits characteristic X-ray powder diffraction patterns as exhibited in FIG. 2.

During the investigation, it was surprisingly found that solvates can also be produced with methanol, ethanol, isopropanol, dichloromethane, acetone, methyl ethyl ketone, and tetrahydrofuran. These solvates can be used to produce the solvent free forms A and B of 5-methyl-pyridine-2-sulfonic acid [6-methoxy-5-(2-methoxy-phenoxy)-2-pyridin-4-yl-pyrimidin-4-yl]-amide. For example, desolvation of the methanol and dichloromethane solvates may be used to obtain form A, and form A may be transformed into form B. The novel solvates form further objects of the invention.

Accordingly, a further object of the invention is a crystalline pseudo-polymorph of 5-methyl-pyridine-2-sulfonic acid

[6-methoxy-5-(2-methoxy-phenoxy)-2-pyridin-4-yl-pyrimidin-4-yl]-amide, which exhibits a characteristic X-ray powder diffraction pattern (as shown in FIG. 3) with characteristic peaks expressed in d-values (Å) measured with a conventional powder X-ray diffractometer using $Cu_{K\alpha}$ radiation: 9.0 (vs), 8.1 (m), 6.4 (s), 5.46 (m), 5.29 (s), 4.77 (m), 4.55 (m), 4.38 (s), 4.26 (m), 4.14 (m), 4.08 (m), 4.02 (m), 3.87 (s), 3.70 (vs), 3.48 (vs), 3.28 (m), 3.13 (m) and 3.04 (m) (according to Table 3) in the form of the ethanol solvate, which is hereinafter designated as form D. The content of ethanol may be from 0.7 to 1.2 mol, referred to 5-methyl-pyridine-2-sulfonic acid [6-methoxy-5-(2-methoxy-phenoxy)-2-pyridin-4-yl-pyrimidin-4-yl]-amide.

Another object of the invention is a crystalline pseudopolymorph of 5-methyl-pyridine-2-sulfonic acid [6-methoxy-5-(2-methoxy-phenoxy)-2-pyridin-4-yl-pyrimidin-4-yl]-amide, which exhibits a characteristic X-ray powder diffraction pattern (as shown in FIG. 4) with characteristic peaks expressed in d-values (Å) measured with a conventional powder X-ray diffractometer using $Cu_{K\alpha}$ radiation: 13.0 (w), 9.1 (vs), 7.9 (m), 6.2 (m), 5.61 (m), 5.51 (w), 5.06 (m), 4.75 (m), 4.57 (m), 4.40 (m), 4.34 (m), 4.17 (m), 3.88 (s), 3.56 (s), 3.32 (m) and 3.05 (m) (according to Table 4) in the form of the acetone hemi solvate, which is hereinafter designated as form E. The content of acetone may be from 0.3 to 0.6 mol, referred to 5-methyl-pyridine-2-sulfonic acid [6-methoxy-5-(2-methoxy-phenoxy)-2-pyridin-4-yl-pyrimidin-4-yl]-amide.

Another object of the invention is a crystalline pseudopolymorph of 5-methyl-pyridine-2-sulfonic acid [6-methoxy-5-(2-methoxy-phenoxy)-2-pyridin-4-yl-pyrimidin-4-yl]-amide which exhibits a characteristic X-ray powder diffraction pattern (as shown in FIG. 5) with characteristic peaks expressed in d-values (Å) measured with a conventional powder X-ray diffractometer using $Cu_{K\alpha}$ radiation: 9.2 (vs), 8.3 (m), 7.8 (m), 6.4 (m), 6.3 (m), 5.75 (m), 5.27 (m), 4.89 (m), 4.62 (m), 4.53 (m), 4.39 (m), 4.22 (m), 4.06 (m), 3.99 (m), 3.83 (m), 3.71 (s), 3.52 (s) and 3.23 (m) (according to Table 5) in the form of the tetrahydrofuran solvate, which is hereinafter designated as form F. The content of tetrahydrofurane may be from 0.7 to 1.2 mol, referred to 5-methyl-pyridine-2-sulfonic acid [6-methoxy-5-(2-methoxy-phenoxy)-2-pyridin-4-yl-pyrimidin-4-yl]-amide.

Another object of the invention is a crystalline pseudopolymorph of 5-methyl-pyridine-2-sulfonic acid [6-methoxy-5-(2-methoxy-phenoxy)-2-pyridin-4-yl-pyrimidin-4-yl]-amide, which exhibits a characteristic X-ray powder diffraction pattern (as shown in FIG. 6) with characteristic peaks expressed in d-values (Å) measured with a conventional powder X-ray diffractometer using $Cu_{K\alpha}$ radiation: 9.1 (vs), 7.9 (m), 6.3 (s), 5.49 (m), 5.38 (m), 5.16 (m), 4.72 (s), 4.56 (m), 4.38 (m), 4.27 (m), 4.12 (m), 4.03 (m), 3.86 (s), 3.82 (vs), 3.63 (s), 3.46 (m) and 3.27 (m) (according to Table 6) in the form of the methanol solvate, which is hereinafter designated as form G. The content of methanol may be from 0.7 to 1.2 mol, referred to 5-methyl-pyridine-2-sulfonic acid [6-methoxy-5-(2-methoxy-phenoxy)-2-pyridin-4-yl-pyrimidin-4-yl]-amide.

Another object of the invention is a crystalline pseudopolymorph of 5-methyl-pyridine-2-sulfonic acid [6-methoxy-5-(2-methoxy-phenoxy)-2-pyridin-4-yl-pyrimidin-4-yl]-amide, which exhibits a characteristic X-ray powder diffraction pattern (as shown in FIG. 7) with characteristic peaks expressed in d-values (Å) measured with a conventional powder X-ray diffractometer using $Cu_{K\alpha}$ radiation: 9.1 (s), 8.2 (m), 6.4 (s), 5.32 (s), 4.82 (vs), 4.77 (m), 4.57 (m), 4.41 (s), 4.27 (m), 4.20 (s), 4.11 (m), 4.06 (m), 4.02 (m), 3.90 (s), 3.72 (vs), 3.50 (s), 3.43 (m), 3.16 (m) and 2.74 (m) (according to Table 7) in the form of the isopropanol solvate, which is hereinafter designated as form H. The content of isopropanol may be from 0.7 to 1.2 mol, referred to 5-methyl-pyridine-2-sulfonic acid [6-methoxy-5-(2-methoxy-phenoxy)-2-pyridin-4-yl-pyrimidin-4-yl]-amide.

Another object of the invention is a crystalline pseudopolymorph of 5-methyl-pyridine-2-sulfonic acid [6-methoxy-5-(2-methoxy-phenoxy)-2-pyridin-4-yl-pyrimidin-4-yl]-amide, which exhibits a characteristic X-ray powder diffraction pattern (as shown in FIG. 8) with characteristic peaks expressed in d-values (Å) measured with a conventional powder X-ray diffractometer using $Cu_{K\alpha}$ radiation: 9.1 (vs), 7.9 (m), 6.2 (s), 5.51 (m), 5.32 (m), 5.10 (m), 4.69 (s), 4.54 (m), 4.24 (m), 4.14 (m), 4.01 (m), 3.82 (s), 3.59 (vs), 3.42 (s), 3.25 (s) and 3.03 (m) (according to Table 8) in the form of the dichloromethane solvate, which is hereinafter designated as form I. The content of dichloromethane may be from 0.2 to 0.6 mol, referred to 5-methyl-pyridine-2-sulfonic acid [6-methoxy-5-(2-methoxy-phenoxy)-2-pyridin-4-yl-pyrimidin-4-yl]-amide.

Another object of the invention is a crystalline pseudopolymorph of 5-methyl-pyridine-2-sulfonic acid [6-methoxy-5-(2-methoxy-phenoxy)-2-pyridin-4-yl-pyrimidin-4-yl]-amide, which exhibits a characteristic X-ray powder diffraction pattern (as shown in FIG. 9) with characteristic peaks expressed in d-values (Å) measured with a conventional powder X-ray diffractometer using $Cu_{K\alpha}$ radiation: 9.4 (vs), 7.8 (m), 6.3 (s), 5.13 (m), 5.00 (s), 4.82 (m), 4.69 (m), 4.49 (m), 4.45 (m), 4.23 (s), 4.14 (m), 3.96 (m), 3.88 (vs), 3.57 (vs), 3.41 (m), 3.16 (m), 3.13 (m) and 2.68 (m) (according to Table 9) in the form of the 2-butanone hemi solvate, which is hereinafter designated as form J. The content of 2-butanone may be from 0.3 to 0.6 mol, referred to 5-methyl-pyridine-2-sulfonic acid [6-methoxy-5-(2-methoxy-phenoxy)-2-pyridin-4-yl-pyrimidin-4-yl]-amide.

Since 5-methyl-pyridine-2-sulfonic acid [6-methoxy-5-(2-methoxy-phenoxy)-2-pyridin-4-yl-pyrimidin-4-yl]-amide is sensitive to light, it is preferred that solutions and suspensions are protected from light, in particular when processes are carried out above ambient temperature.

For the preparation of the crystalline forms, there may be used crystallisation techniques well known in the art, such as suspension, precipitation, re-crystallisation, evaporation, water vapor sorption or solvent vapor sorption methods or de-solvation of solvates. Diluted, saturated or super-saturated solutions may be used for crystallisation, with or without seeding with suitable nucleating agents. Temperatures up to the boiling point of the solvent (solvent mixture) and preferably room temperature (15° C. to 30° C.) may be applied to form solutions. Cooling to initiate crystallisation and precipitation down to −50° C. and preferably down to −10° C. to 10° C. may be applied. Meta-stable crystalline forms can be used to prepare solutions or suspensions for the preparation of more stable forms and to achieve higher concentrations in the solutions. Crystal forms such as A or mixtures containing form A, as well as solvates, for example forms D to J, may be used to produce crystal form B. Furthermore, the solvent in any solvated form D to J may be removed by stirring a suspension of a solvate in a non solvate forming solvent to obtain a solvent free form A or B.

A further object of the invention is a process for the preparation of crystalline form A of 5-methyl-pyridine-2-sulfonic acid [6-methoxy-5-(2-methoxy-phenoxy)-2-pyridin-4-yl-pyrimidin-4-yl]-amide, comprising dissolving a salt of 5-methyl-pyridine-2-sulfonic acid [6-methoxy-5-(2-methoxy-phenoxy)-2-pyridin-4-yl-pyrimidin-4-yl]-amide in water or water containing a cosolvent, precipitating the free base by adding an acid, isolating and drying the solid residue.

The salt of 5-methyl-pyridine-2-sulfonic acid [6-methoxy-5-(2-methoxy-phenoxy)-2-pyridin-4-yl-pyrimidin-4-yl]-amide is preferably an alkaline or alkaline earth salt, for example the sodium salt. The process is carried out in a temperature range from 10° C. to 60° C. Isolation of the solid may be done by decantation or filtration. Drying is preferably carried out at about room temperature or at a temperature up to 80° C.

A further object of the invention is a process for the preparation of crystalline form B of 5-methyl-pyridine-2-sulfonic acid [6-methoxy-5-(2-methoxy-phenoxy)-2-pyridin-4-yl-pyrimidin-4-yl]-amide, comprising suspending or dissolving a solid form other than form B of 5-methyl-pyridine-2-sulfonic acid [6-methoxy-5-(2-methoxy-phenoxy)-2-pyridin-4-yl-pyrimidin-4-yl]-amide at a temperature from 20° C. to 100° C. in a solvent, optionally cooling the solution to precipitate 5-methyl-pyridine-2-sulfonic acid [6-methoxy-5-(2-methoxy-phenoxy)-2-pyridin-4-yl-pyrimidin-4-yl]-amide, stirring the suspension for a time sufficient to complete formation of crystal form B, removing the solvent and drying the solid residue. A solid form other than form B encompasses crystal form B, which is contaminated with another form, for example form A or D to J. The process may be carried out with or without seeding.

The temperature range of the suspension/solution may be from 20° C. to 100° C. and preferably from 20° C. to 70° C. Cooling may be carried out continuously or stepwise and cooling rates may be controlled such that the rates are in the range from 0.1° C./h to 5° C./h and preferably from 0.3° C./h to 3° C./h. Cooling may be stopped at a certain lower temperature level and kept at this temperature until crystallisation is completed. The concentration of 5-methyl-pyridine-2-sulfonic acid [6-methoxy-5-(2-methoxy-phenoxy)-2-pyridin-4-yl-pyrimidin-4-yl]-amide in the suspension may be from 60 to 600 mg/ml and preferably from 80 to 450 mg/ml solvent, depending on temperature. Suitable solvents are solvents which are essentially free of water and which do not form a solvated form of high stability, for example methyl tert.-butyl ether, acetone, acetonitrile and hexane and mixtures thereof. Preferred is methyl tert.-butyl ether which is essentially free of water. Essentially free of water means in the context of the invention that the solvent contains not more than 2 and preferably not more than 0.5 percent by weight of water, referred to the solvent. Stirring time may be from 1 hour to 5 days. Isolation of the solid may be done by decantation or filtration. Drying is preferably carried out at about room temperature or at a temperature up to 60° C.

Still a further object of the invention is a process for the manufacture of 5-methyl-pyridine-2-sulfonic acid [6-methoxy-5-(2-methoxy-phenoxy)-2-pyridin-4-yl-pyrimidin-4-yl]-amide of crystal form B, comprising heating form A or a mixture of forms A and B of 5-methyl-pyridine-2-sulfonic acid [6-methoxy-5-(2-methoxy-phenoxy)-2-pyridin-4-yl-pyrimidin-4-yl]-amide, preferably under a protective atmosphere, to a temperature of 80° C. to 160° C., preferably 100° C. to 160° C., with optional mixing for a time sufficient to form crystal form B.

The temperature for the process is most preferred between 100° C. and 120° C. In order to ensure better heat exchange it is preferred to carry out the process with powder beds not exceeding 10 cm, most preferably not exceeding 5 cm. In addition, metal, for example aluminum, inserts may be used to better distribute the heat within the powder.

The crystal forms A and D to J may be used in pharmaceutical compositions and more preferably as intermediates and starting materials to produce the particularly preferred form B, which can be easily processed and handled due to its stability, possibility for preparation by targeted conditions, its suitable morphology and particle size. These outstanding properties renders polymorph form B especially feasible for pharmaceutical applications.

Accordingly, this invention is also directed to a pharmaceutical composition comprising the crystal forms A, B and D to J of 5-methyl-pyridine-2-sulfonic acid [6-methoxy-5-(2-methoxy-phenoxy)-2-pyridin-4-yl-pyrimidin-4-yl]-amide and a pharmaceutically acceptable carrier or diluent.

In a preferred embodiment, this invention is also directed to a pharmaceutical composition comprising the crystal form B of 5-methyl-pyridine-2-sulfonic acid [6-methoxy-5-(2-methoxy-phenoxy)-2-pyridin-4-yl-pyrimidin-4-yl]-amide and a pharmaceutically acceptable carrier or diluent.

The amount of crystal forms of 5-methyl-pyridine-2-sulfonic acid [6-methoxy-5-(2-methoxy-phenoxy)-2-pyridin-4-yl-pyrimidin-4-yl]-amide substantially depends on type of formulation and desired dosages during administration time periods. The amount in an oral formulation may be from 0.1 to 50 mg, preferably from 0.5 to 30 mg, and more preferably from 1 to 15 mg.

Oral formulations may be solid formulations such as capsules, tablets, pills and troches, or liquid formulations such as aqueous suspensions, elixirs and syrups. Solid and liquid formulations encompass also incorporation of the crystal forms of 5-methyl-pyridine-2-sulfonic acid [6-methoxy-5-(2-methoxy-phenoxy)-2-pyridin-4-yl-pyrimidin-4-yl]-amide according to the invention into liquid or solid food. Liquids also encompass solutions of form A of 5-methyl-pyridine-2-sulfonic acid [6-methoxy-5-(2-methoxy-phenoxy)-2-pyridin-4-yl-pyrimidin-4-yl]-amide for parenteral applications such as infusion or injection.

The crystal forms according to the invention may be directly used as powders (micronized particles), granules, suspensions or solutions, or they may be combined together with other pharmaceutically acceptable ingredients in admixing the components and optionally finely divide them, and then filling capsules, composed for example from hard or soft gelatine, compressing tablets, pills or troches, or suspend or dissolve them in carriers for suspensions, elixirs and syrups. Coatings may be applied after compression to form pills.

Pharmaceutically acceptable ingredients are well known for the various types of formulation and may be for example binders such as natural or synthetic polymers, excipients, lubricants, surfactants, sweetening and flavouring agents, coating materials, preservatives, dyes, thickeners, adjuvants, antimicrobial agents and carriers for the various formulation types.

Examples for binders are gum tragacanth, acacia, starch, gelatine, and biological degradable polymers such as homo- or co-polyesters of dicarboxylic acids, alkylene glycols, poly-alkylene glycols and/or aliphatic hydroxyl carboxylic acids; homo- or co-polyamides of dicarboxylic acids, alkylene diamines, and/or aliphatic amino carboxylic acids; corresponding polyester-polyamide-co-polymers, polyanhydrides, polyorthoesters, polyphosphazene and polycarbonates. The biological degradable polymers may be linear, branched or crosslinked. Specific examples are poly-glycolic acid, poly-lactic acid, and poly-d,l-lactide/glycolide. Other examples for polymers are water-soluble polymers such as polyoxaalkylenes (polyoxaethylene, polyoxapropylene and mixed polymers thereof, poly-acrylamides and hydroxylalkylated polyacrylamides, poly-maleic acid and esters or -amides thereof, poly-acrylic acid and esters or -amides thereof, poly-vinylalcohol und esters or -ethers thereof, poly-vinylimidazole, poly-vinylpyrrolidon, und natural polymers like chitosan.

Examples for excipients are phosphates such as dicalcium phosphate.

Examples for lubricants are natural or synthetic oils, fats, waxes, or fatty acid salts like magnesium stearate.

Surfactants may be anionic, anionic, amphoteric or neutral. Examples for surfactants are lecithin, phospholipids, octyl sulfate, decyl sulfate, dodecyl sulfate, tetradecyl sulfate, hexadecyl sulfate and octadecyl sulfate, Na oleate or Na caprate, 1-acylaminoethane-2-sulfonic acids, such as 1-octanoylaminoethane-2-sulfonic acid, 1-decanoylaminoethane-2-sulfonic acid, 1-dodecanoylaminoethane-2-sulfonic acid, 1-tetradecanoylaminoethane-2-sulfonic acid, 1-hexadecanoylaminoethane-2-sulfonic acid, and 1-octadecanoylaminoethane-2-sulfonic acid, and taurocholic acid and taurodeoxycholic acid, bile acids and their salts, such as cholic acid, deoxycholic acid and sodium glycocholates, sodium caprate or sodium laurate, sodium oleate, sodium lauryl sulphate, sodium cetyl sulphate, sulfated castor oil and sodium dioctylsulfosuccinate, cocamidopropylbetaine and laurylbetaine, fatty alcohols, cholesterols, glycerol mono- or -distearate, glycerol mono- or -dioleate and glycerol mono- or -dipalmitate, and polyoxyethylene stearate.

Examples for sweetening agents are sucrose, fructose, lactose or aspartam.

Examples for flavouring agents are peppermint, oil of wintergreen or fruit flavours like cherry or orange flavour.

Examples for coating materials gelatine, wax, shellac, sugar or biological degradable polymers.

Examples for preservatives are methyl or propylparabens, sorbic acid, chlorobutanol, phenol and thimerosal.

Examples for adjuvants are fragrances.

Examples for thickeners are synthetic polymers, fatty acids and fatty acid salts and esters and fatty alcohols.

Examples for liquid carriers are water, alcohols such as ethanol, glycerol, propylene glycol, liquid polyethylene glycols, triacetin and oils. Examples for solid carriers are talc, clay, micro-crystalline cellulose, silica, alumina and the like.

The formulation according to the invention may also contain isotonic agents, such as sugars, buffers or sodium chloride.

The crystal form according to the invention may also be formulated as effervescent tablet or powder, which disintegrate in an aqueous environment to provide a drinking solution.

A syrup or elixir may contain the polymorph of the invention, sucrose or fructose as sweetening agent a preservative like methylparaben, a dye and a flavouring agent.

Slow release formulations may also be prepared from the crystal form according to the invention in order to achieve a controlled release of the active agent in contact with the body fluids in the gastro intestinal tract, and to provide a substantial constant and effective level of the active agent in the blood plasma. The crystal forms may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

The crystal forms of the invention are also useful for administering a combination of therapeutic effective agents to a mammal, such as a human. Such a combination therapy can be carried out in using at least one further therapeutic agent which can be additionally dispersed or dissolved in a formulation.

The crystal forms of this invention and its formulations respectively can be also administered in combination with other therapeutic agents that are effective to treat a given condition to provide a combination therapy.

The crystal forms and the pharmaceutical composition according to the invention are highly suitable for effective treatment in the field of heart failure (acute and chronic), systemic and pulmonary hypertension, acute ischaemic coronary syndrome, angina pectoris, renal failure (acute and chronic), diabetic nephropathy, organic transplant (e.g. liver, heart, kidney), cyclosporine nephrotoxicity, vasospastic disease (subarachnoid haemorrhage but also haemorragic and non-haemorragic stroke, Raynaud syndrome), peripheral artery occlusive disease, prevention of restenosis after stent or balloon angioplasty, septic shock or multiple organ failure as that occurring in intensive care, asthma, chronic obstructive pulmonary disease, gastric and duodenal ulcus, liver cirrhosis, pancreatitis (acute and chronic), inflammatory bowel disease, fibrosis, atheriosclerosis, obesity, glaucoma, prostatic adenoma, migraine, erectile dysfunction, adjunct to cancer therapy as well as other disorders associated with endothelin activities.

An object of the invention is also a therapeutic method for producing an endothelial antagonistic effect in a mammal comprising administering to a mammal in need of such therapy, an effective amount of a crystal form of 5-methyl-pyridine-2-sulfonic acid [6-methoxy-5-(2-methoxy-phenoxy)-2-pyridin-4-yl-pyrimidin-4-yl]-amide according to the invention.

Another object of the invention is a method of delivering a crystal form of 5-methyl-pyridine-2-sulfonic acid [6-methoxy-5-(2-methoxy-phenoxy)-2-pyridin-4-yl-pyrimidin-4-yl]-amide according to the invention to a host, comprising administering to a host an effective amount of a crystal form according to the invention.

A further object of the invention is the use of a crystal form according to the invention for the manufacture of a medicament useful in the treatment in the field of heart failure (acute and chronic), systemic and pulmonary hypertension, acute ischaemic coronary syndrome, angina pectoris, renal failure (acute and chronic), diabetic nephropathy, organic transplant (e.g. liver, heart, kidney), cyclosporine nephrotoxicity, vasospastic disease (subarachnoid haemorrhage but also haemorragic and non-haemorragic stroke, Raynaud syndrome), peripheral artery occlusive disease, prevention of restenosis after stent or balloon angioplasty, septic shock or multiple organ failure as that occurring in intensive care, asthma, chronic obstructive pulmonary disease, gastric and duodenal ulcus, liver cirrhosis, pancreatitis (acute and chronic), inflammatory bowel disease, fibrosis, atheriosclerosis, obesity, glaucoma, prostatic adenoma, migraine, erectile dysfunction, adjunct to cancer therapy as well as other disorders associated with endothelin activities in a mammal, such as a human; and a crystal form according to the invention for use in medical therapy.

The following examples illustrate the invention.

The compound 5-methyl-pyridine-2-sulfonic acid [6-methoxy-5-(2-methoxy-phenoxy)-2-pyridin-4-yl-pyrimidin-4-yl]-amide is hereinafter designated as SPP301.

Experimental:

Powder X-ray Diffraction (PXRD): PXRD is performed on a Philips 1710 powder X-ray diffractometer using $Cu_{K\alpha}$ radiation. D-spacings are calculated from the 2θ using the wave-length of the $Cu_{K\alpha1}$ radiation of 1.54060 A. The X-ray tube was operated at a Voltage of 45 kV, and a current of 45 mA. A step size of 0.02°, and a counting time of 2.4 s per step is applied. Generally, 2θ values are within an error of ±0.1-0.2°. The experimental error on the d-spacing values is therefore dependent on the peak location.

TG-FTIR: Thermogravimetric measurements are carried out with a Netzsch Thermo-Micro-balance TG 209 coupled to a Bruker FTIR Spectrometer Vector 22 (sample pans with a pinhole, $N_2$ atmosphere, heating rate 10 K/min).

Raman spectroscopy: FT-Raman spectra are recorded on a Bruker RFS 100 FT-Raman system with a near infrared Nd:YAG laser operating at 1064 nm and a liquid nitrogen-cooled germanium detector. For each sample, 64 scans with a resolution of 2 $cm^{-1}$ are accumulated. Generally, 200 mW laser power is used.

EXAMPLE 1

840 g of SPP301 in form of a mixture of forms A and B are placed in a 4 liter glass reactor. In order to ensure a good heat transport, the reactor is equipped with aluminum sheet metal inserts which reduce the lengths of the powder beds to about 5 cm. The reactor is placed in an oven. The void volume of the glass reactor is five times purged with pure nitrogen by subsequent evacuation and purging cycles. At the end of the cycles the reactor is filled with dry nitrogen to a pressure of 900 mbar. Then the oven temperature is slowly raised to 120° C. and kept at this temperature for 6 hours, before the oven is turned off and the temperature is reduced to room temperature within about 4 hours. Characterization of the crystalline material by powder X-ray diffraction shows that SPP301 pure form B is obtained, i.e. a powder X-ray diffraction pattern as shown in Table 2 and in FIG. 2 is found.

EXAMPLE 2

165 mg of a 1:1 mixture of SPP301 forms A and B are suspended in 2.0 ml acetone (Fluka no. 0570, analytical grade, essentially free of water) in a 4.0 ml amber glass vial. The obtained suspension is stirred at room temperature for about 60 hours, then the solid is separated by filtration, and dried at 40° C. under reduced pressure for 2 hours. Characterization of the crystalline material by powder X-ray diffraction shows that SPP301 pure form B is obtained, i.e. a powder X-ray diffraction pattern as shown in FIG. 2 is found.

EXAMPLE 3

200 mg of SPP301 form A which is previously dried, are suspended in 2.0 ml methyl tert. butyl ether (analytical grade, essentially free of water) in a 4.0 ml amber glass vial. To the obtained suspension 5 mg of form B seed crystals are added, and the suspension is stirred at 40° C. for about 20 hours, then the solid is separated by filtration, and dried at 40° C. under reduced pressure for 2 hours. Characterization of the crystalline material by powder X-ray diffraction shows that SPP301 pure form B is obtained, i.e. a powder X-ray diffraction pattern as shown in FIG. 2 is found. Further analysis by GC-head space shows that the obtained crystalline form is essentially free of residual solvent.

EXAMPLE 4

479.5 mg (1 mmol) of SPP301 form B are dissolved in 10 ml of aqueous 0.1 M NaOH solution and 9 ml of water in a 40.0 ml amber glass vial. The obtained solution is filtered through a 0.22 μm filtration unit and then neutralized with 1.0 ml of 1M hydrochloric acid, which is slowly added under stirring at room temperature. After stirring the obtained suspension at room temperature for about 2 hours, the obtained precipitate is separated by filtration, and the solid crystalline material is dried under reduced pressure at 60° C. for about 4 hours. Characterization of the crystalline material by powder X-ray diffraction shows that SPP301 form A is obtained, i.e. a powder X-ray diffraction pattern as shown in Table 1 and in FIG. 1 is found.

EXAMPLE 5

200 mg of SPP301 form G (methanol solvate) as obtained in Example 9 are dried under nitrogen at room temperature for 4 hours and then under reduced pressured in an oven at 60° C. for about 16 hours. Characterization of the new crystalline material by powder X-ray diffraction shows that SPP301 pure form A is obtained, i.e. a powder X-ray diffraction pattern as shown in FIG. 1 is found.

EXAMPLE 6

65 mg of SPP301 form B are suspended in a mixture of 500 μl ethanol (Fluka no. 02860) and 500 μl acetone (Fluka no. 0570) in 4.0 ml amber glass vial. The resulting suspension is stirred at room temperature for about 16 hours before the solid material is separated by filtration. The filtered solid is washed with 1.0 ml of ethanol, and then dried in air for about 2 hours. Characterization of the crystalline material by powder X-ray diffraction shows that SPP301 form D (ethanol solvate) is obtained, i.e. a powder X-ray diffraction pattern as shown in Table 3 and in FIG. 3 is found. Analysis by thermogravimetry coupled with infrared spectroscopy shows that form D contains about 8.7% of ethanol.

EXAMPLE 7

126 mg of SPP301 form A are suspended in 2.0 ml of acetone (Fluka no. 0570) in a 4.0 ml amber glass vial. The resulting suspension is stirred at room temperature for about 44 hours, and the obtained solid is dried in air at room temperature for about one hour. Characterization of the crystalline material by powder X-ray diffraction shows that SPP301 form E (acetone hemi solvate) is obtained, i.e. a powder X-ray diffraction pattern as shown in Table 4 and in FIG. 4 is found. Analysis by thermogravimetry coupled with infrared spectroscopy shows that form E contains about 5% of acetone.

EXAMPLE 8

52 mg of SPP301 form B are suspended in 1.0 ml tetrahydrofuran (THF, Fluka no. 87368) in a 4.0 ml amber glass vial and the resulting suspension is stirred at 23° C. for about 20 hours before the solid is separated by filtration. The obtained crystalline material is dried in air at room temperature for about one hour. Characterization of the crystalline material by powder X-ray diffraction shows that SPP301 form F (THF solvate) is obtained, i.e. a powder X-ray diffraction pattern as shown in Table 5 and in FIG. 5 is found. Analysis by thermogravimetry coupled with infrared spectroscopy shows that form F contains about 11.7% of THF.

EXAMPLE 9

880 mg of SPP301 form B are suspended in 9.3 ml of methanol (Fluka, analytical grade) in a 22 ml amber glass flask. The resulting suspension is stirred at room temperature for about 44 hours before the solid is separated by filtration and dried under nitrogen at room temperature for about one hour. Characterization of the crystalline material by powder X-ray diffraction shows that SPP301 form G (methanol solvate) is obtained, i.e. a powder X-ray diffraction pattern as shown in Table 6 and in FIG. 6 is found. Analysis by thermogravimetry coupled with infrared spectroscopy shows that form G contains about 4.9% of methanol.

EXAMPLE 10

29 mg of SPP301 form B and 26 mg of SPP301 form A are suspended in a mixture of 500 μl acetone and 500 μl isopropanol (Fluka no. 59300) in a 4.0 ml amber glass vial and the resulting suspension is stirred at 23° C. for about 70 hours. Then suspension is filtered and the obtained solid dried in air at 23° C. for about one hour. Characterization of the crystalline material by powder X-ray diffraction shows that SPP301 form H (isopropanol solvate) is obtained, i.e. a powder X-ray diffraction pattern as shown in Table 7 and in FIG. 7 is found. Analysis by thermogravimetry coupled with infrared spectroscopy shows that form H contains about 10.4% of isopropanol.

EXAMPLE 11

A mixture of 34 mg SPP301 form B and 34 mg SPP301 form A is suspended in 1.0 ml of dichloromethane in a 4.0 ml amber glass vial. The resulting suspension is stirred at 23° C. for about 70 hours before the solid is separated by filtration, and the obtained crystalline material is dried in air at 23° C. for about one hour. Characterization of the crystalline material by powder X-ray diffraction shows that SPP301 form I (dichloromethane (hemi) solvate) is obtained, i.e. a powder X-ray diffraction pattern as shown in Table 8 and in FIG. 8 is found. Analysis by thermogravimetry coupled with infrared spectroscopy shows that form I contains about 6.0% of dichloromethane.

EXAMPLE 12

105 mg of SPP301 form A are suspended in 1.0 methyl ethyl ketone (Fluka no. 4380) in a 4.0 ml amber glass vial. The resulting suspension is stirred at 20° C. for about 88 hours before the solid is separated by filtration. The obtained crystalline material is dried in air at room temperature for about one hour. Characterization of the crystalline material by powder X-ray diffraction shows that SPP301 form J (2-butanone hemi solvate) is obtained, i.e. a powder X-ray diffraction pattern as shown in Table 9 and in FIG. 9 is found. Analysis by thermogravimetry shows that form J contains about 6.7% of residual solvent which is attributed to methyl ethyl ketone.

TABLE 1

D-Spacing Table for Form A

Figure 1:
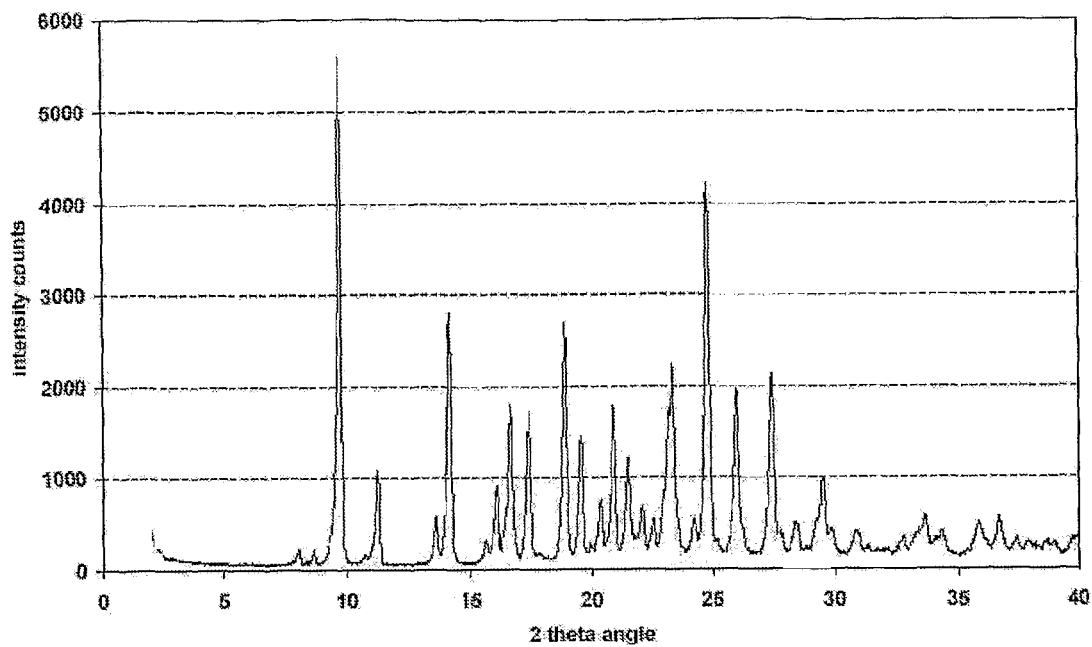
FIG. 1: Powder X-ray Diffraction Pattern of Form A
Figure 2:
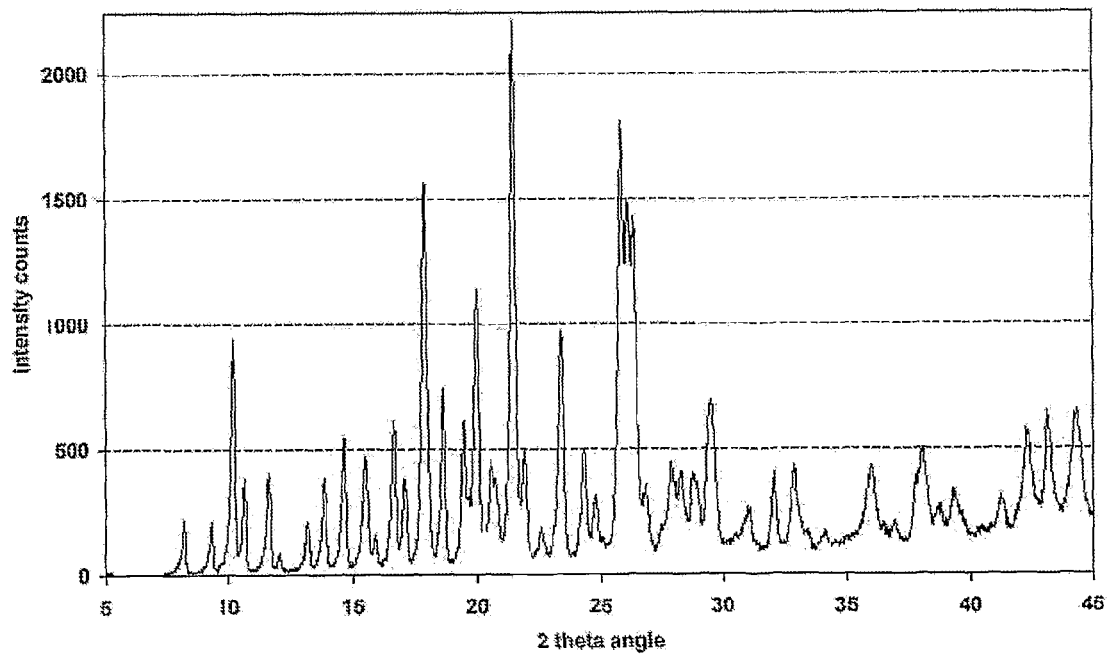
FIG. 2: Powder X-ray Diffraction Pattern of Form B
Figure 3:
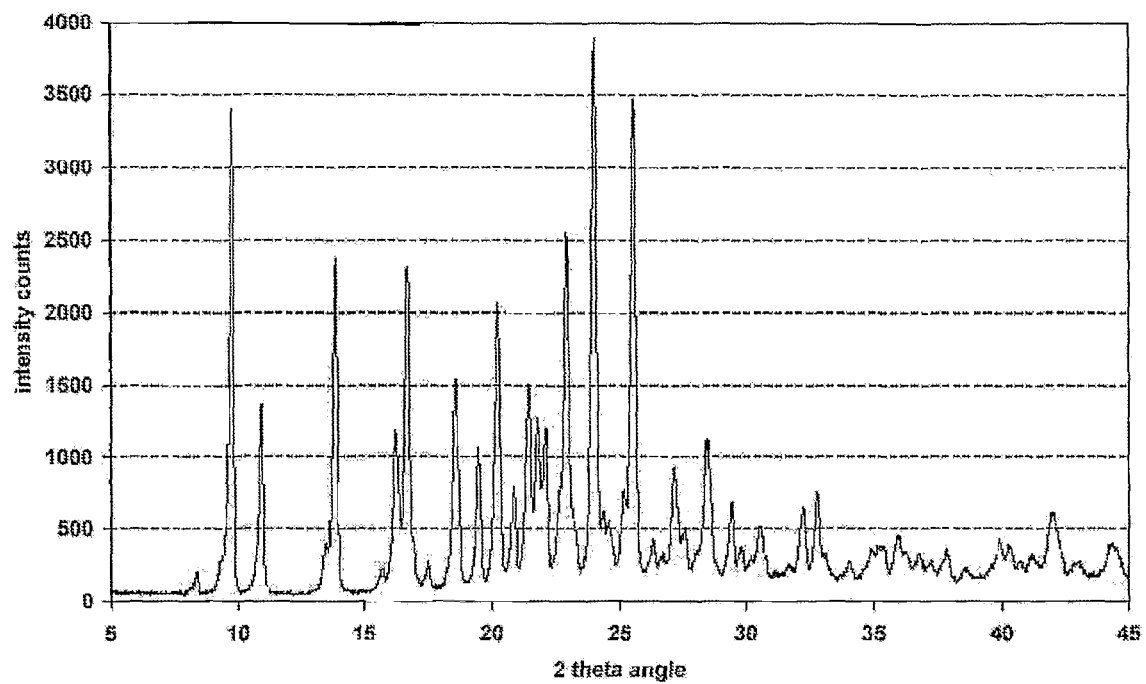
FIG. 3: Powder X-ray Diffraction Pattern of Form D
Figure 4:
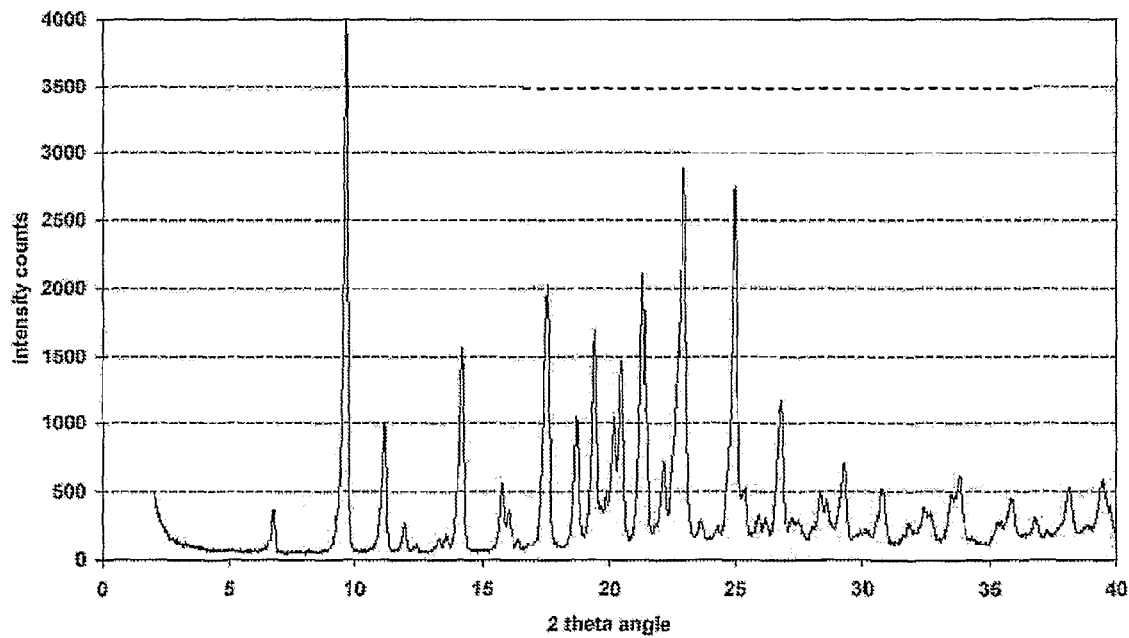
FIG. 4: Powder X-ray Diffraction Pattern of Form E
Figure 5:
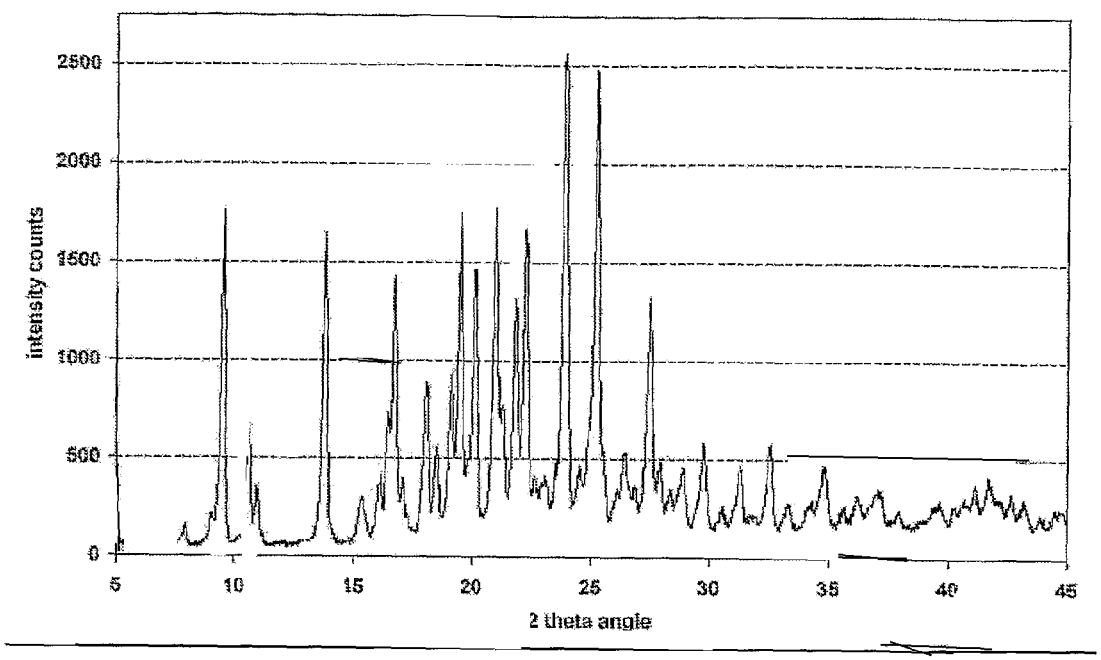
FIG. 5: Powder X-ray Diffraction Pattern of Form F
Figure 6:
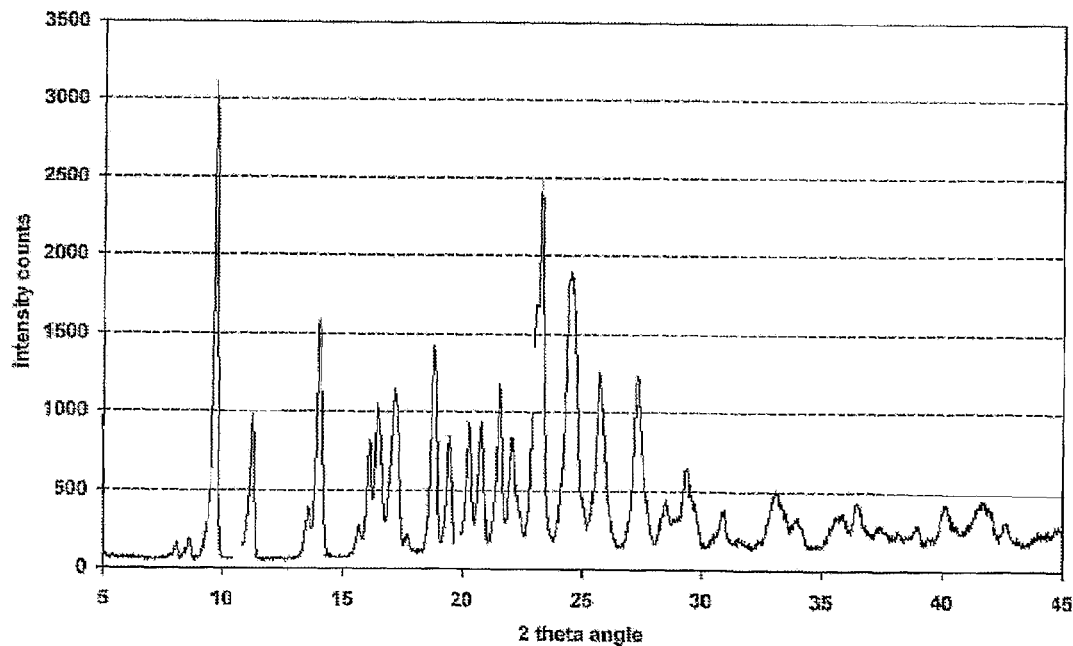
FIG. 6: Powder X-ray Diffraction Pattern of Form G
Figure 7:
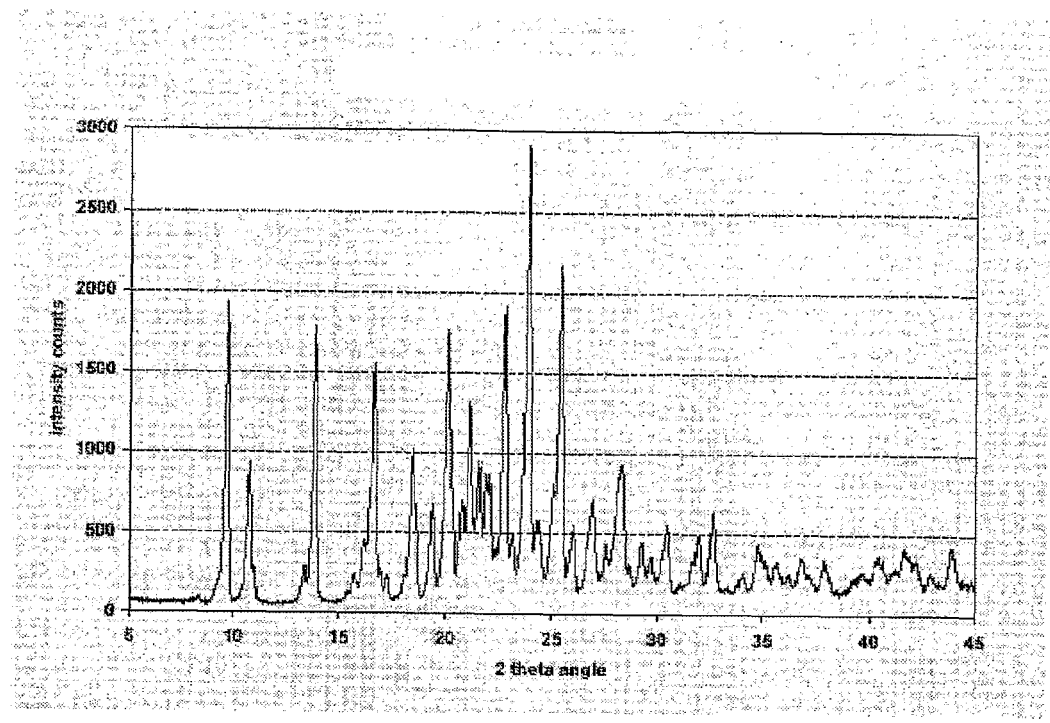
FIG. 7: Powder X-ray Diffraction Pattern of Form H
Figure 8:
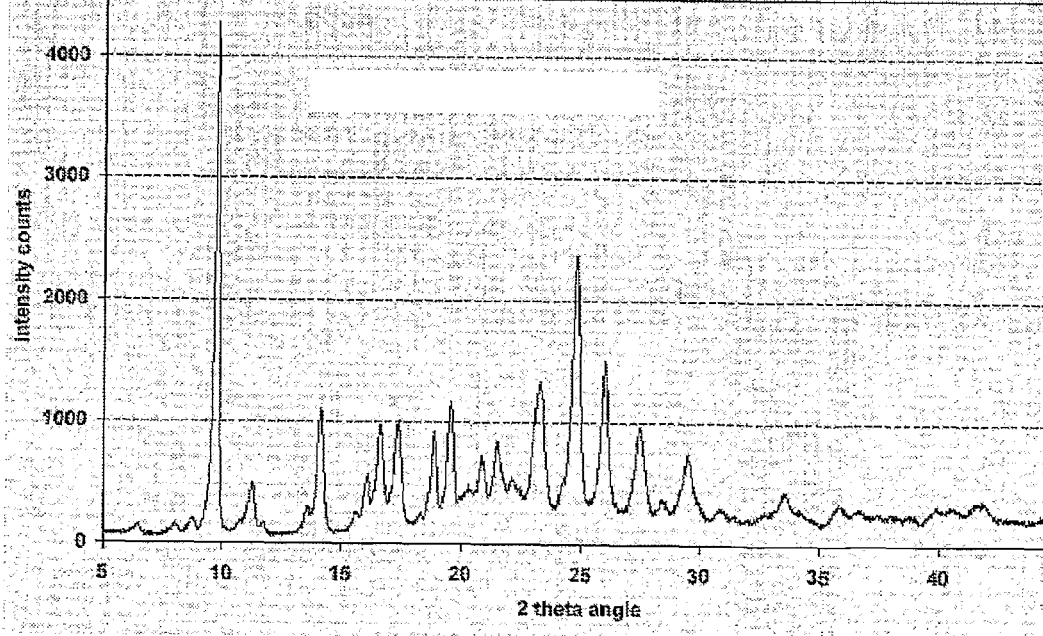
FIG. 8: Powder X-ray Diffraction Pattern of Form I
Figure 9:
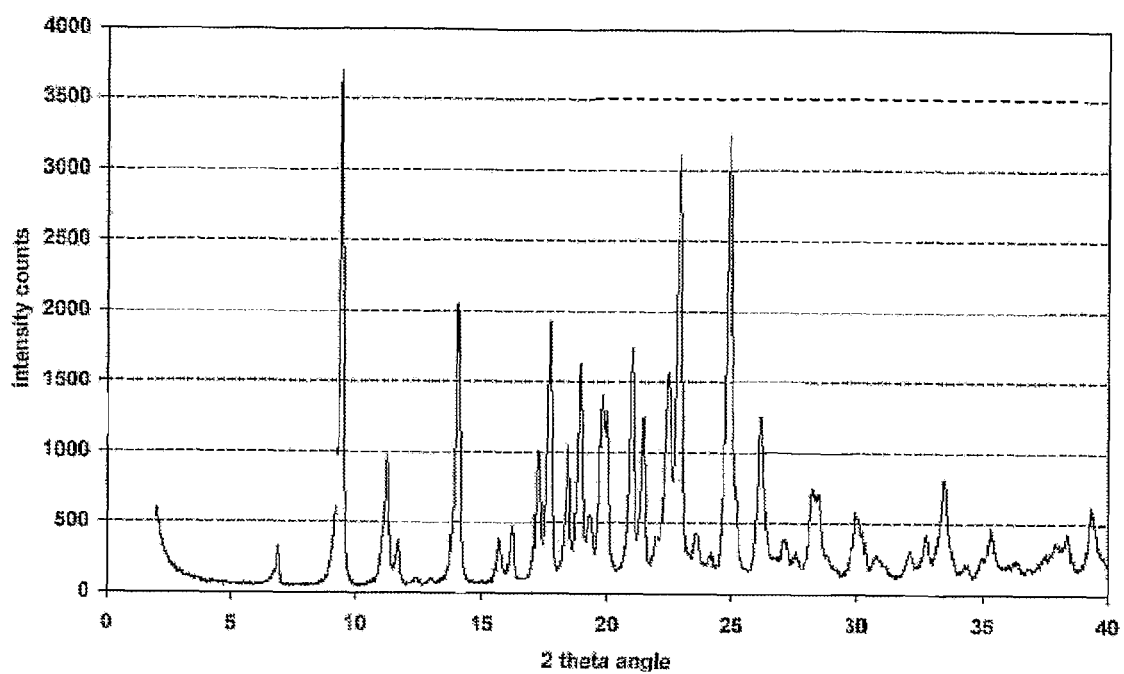
FIG. 9: Powder X-ray Diffraction Pattern of Form J Tables of X-ray diffraction patterns.

| Pos. [°2Th.] | d-value [Å] | Rel. Int. |
| --- | --- | --- |
| 8.1 | 10.9 | vw |
| 8.8 | 10.1 | vw |
| 9.8 | 9.0 | vs |
| 10.7 | 8.2 | vw |
| 11.3 | 7.8 | m |
| 13.7 | 6.5 | w |
| 14.3 | 6.2 | s |
| 15.7 | 5.65 | vw |
| 16.2 | 5.48 | m |
| 16.7 | 5.30 | m |
| 17.5 | 5.07 | m |
| 19.0 | 4.67 | s |
| 19.6 | 4.52 | m |
| 20.0 | 4.44 | vw |
| 20.4 | 4.34 | w |
| 21.0 | 4.23 | m |
| 21.5 | 4.14 | m |
| 22.2 | 4.00 | w |
| 22.7 | 3.91 | w |
| 23.2 | 3.83 | m |
| 23.4 | 3.79 | m |
| 24.2 | 3.67 | vw |
| 24.9 | 3.57 | s |
| 26.1 | 3.42 | m |
| 27.6 | 3.23 | m |
| 28.4 | 3.14 | vw |
| 29.6 | 3.02 | m |
| 30.0 | 2.98 | vw |
| 31.0 | 2.88 | vw |
| 31.4 | 2.85 | vw |
| 32.7 | 2.74 | vw |
| 33.3 | 2.69 | vw |
| 33.8 | 2.66 | w |
| 34.4 | 2.60 | vw |

TABLE 2

D-Spacing Table for Form B

| Pos. [°2Th.] | d-value [Å] | Rel. Int. |
| --- | --- | --- |
| 8.2 | 10.7 | m |
| 9.4 | 9.4 | m |
| 10.2 | 8.6 | vs |
| 10.7 | 8.3 | m |
| 11.7 | 7.6 | m |
| 12.1 | 7.3 | vw |
| 13.2 | 6.7 | m |
| 13.9 | 6.4 | m |
| 14.7 | 6.0 | m |
| 15.6 | 5.69 | m |
| 16.0 | 5.55 | w |
| 16.7 | 5.30 | m |
| 17.1 | 5.17 | m |
| 17.9 | 4.95 | vs |
| 18.7 | 4.76 | m |
| 19.5 | 4.56 | m |
| 20.0 | 4.43 | s |
| 20.6 | 4.32 | m |
| 20.7 | 4.28 | m |
| 21.5 | 4.13 | vs |
| 21.9 | 4.05 | m |
| 22.6 | 3.93 | vw |
| 23.4 | 3.80 | s |
| 24.4 | 3.65 | m |
| 24.8 | 3.59 | w |
| 25.9 | 3.45 | s |
| 26.1 | 3.41 | s |
| 26.4 | 3.37 | s |

TABLE 2-continued

D-Spacing Table for Form B

| Pos. [°2Th.] | d-value [Å] | Rel. Int. |
|---|---|---|
| 26.9 | 3.32 | w |
| 27.9 | 3.20 | w |
| 28.3 | 3.15 | w |
| 28.8 | 3.10 | w |
| 29.5 | 3.03 | m |
| 31.1 | 2.88 | vw |
| 32.1 | 2.79 | w |
| 32.9 | 2.72 | w |
| 33.5 | 2.68 | vw |
| 34.2 | 2.62 | vw |

TABLE 3

D-Spacing Table for Form D (Ethanol Solvate)

| Pos. [°2Th.] | d-value [Å] | Rel. Int. |
|---|---|---|
| 8.4 | 10.6 | vw |
| 9.8 | 9.0 | vs |
| 11.0 | 8.1 | m |
| 13.5 | 6.6 | w |
| 13.9 | 6.4 | s |
| 15.8 | 5.62 | vw |
| 16.2 | 5.46 | m |
| 16.8 | 5.29 | s |
| 17.6 | 5.05 | vw |
| 18.6 | 4.77 | m |
| 19.5 | 4.55 | m |
| 20.3 | 4.38 | s |
| 20.9 | 4.26 | m |
| 21.5 | 4.14 | m |
| 21.8 | 4.08 | m |
| 22.1 | 4.02 | m |
| 22.6 | 3.93 | m |
| 23.0 | 3.87 | s |
| 24.0 | 3.70 | vs |
| 24.3 | 3.66 | w |
| 24.6 | 3.62 | w |
| 25.2 | 3.54 | m |
| 25.6 | 3.48 | vs |
| 26.3 | 3.38 | w |
| 26.7 | 3.34 | vw |
| 27.2 | 3.28 | m |
| 27.6 | 3.23 | w |
| 28.5 | 3.13 | m |
| 29.4 | 3.04 | m |
| 29.8 | 3.00 | vw |
| 30.6 | 2.92 | w |
| 30.8 | 2.90 | vw |
| 31.7 | 2.82 | vw |
| 32.3 | 2.77 | m |
| 32.8 | 2.73 | m |
| 34.1 | 2.63 | vw |
| 34.9 | 2.57 | w |

TABLE 4

D-Spacing Table for Form E (Acetone Solvate)

| Pos. [°2Th.] | d-value [Å] | Rel. Int. |
|---|---|---|
| 6.8 | 13.0 | w |
| 9.7 | 9.1 | vs |
| 11.2 | 7.9 | m |
| 12.0 | 7.4 | w |
| 12.4 | 7.1 | vw |
| 13.3 | 6.7 | vw |
| 13.6 | 6.5 | vw |
| 14.2 | 6.2 | m |
| 15.8 | 5.61 | m |

TABLE 4-continued

D-Spacing Table for Form E (Acetone Solvate)

| Pos. [°2Th.] | d-value [Å] | Rel. Int. |
|---|---|---|
| 16.1 | 5.51 | w |
| 16.4 | 5.42 | vw |
| 17.5 | 5.06 | m |
| 18.7 | 4.75 | m |
| 19.4 | 4.57 | m |
| 19.9 | 4.47 | w |
| 20.2 | 4.40 | m |
| 20.5 | 4.34 | m |
| 21.3 | 4.17 | m |
| 22.2 | 4.01 | m |
| 22.9 | 3.88 | s |
| 23.6 | 3.76 | vw |
| 24.3 | 3.67 | vw |
| 25.0 | 3.56 | s |
| 25.4 | 3.50 | w |
| 25.9 | 3.43 | vw |
| 26.2 | 3.40 | vw |
| 26.8 | 3.32 | m |
| 27.2 | 3.28 | vw |
| 27.5 | 3.24 | vw |
| 28.4 | 3.14 | w |
| 28.6 | 3.12 | w |
| 29.3 | 3.05 | m |
| 30.8 | 2.91 | w |
| 31.9 | 2.81 | vw |
| 32.4 | 2.76 | w |
| 32.7 | 2.74 | w |
| 33.5 | 2.68 | w |
| 33.8 | 2.65 | m |

TABLE 5

D-Spacing Table for Form F (THF Solvate)

| Pos. [°2Th.] | d-value [Å] | Rel. Int. |
|---|---|---|
| 7.9 | 11.1 | vw |
| 9.6 | 9.2 | vs |
| 10.3 | 8.6 | vw |
| 10.7 | 8.3 | m |
| 11.0 | 8.0 | w |
| 11.3 | 7.8 | m |
| 13.9 | 6.4 | m |
| 14.2 | 6.3 | m |
| 15.4 | 5.75 | m |
| 16.2 | 5.47 | w |
| 16.8 | 5.27 | m |
| 17.1 | 5.17 | w |
| 18.1 | 4.89 | m |
| 18.6 | 4.76 | w |
| 19.2 | 4.62 | m |
| 19.6 | 4.53 | m |
| 20.2 | 4.39 | m |
| 21.0 | 4.22 | m |
| 21.9 | 4.06 | m |
| 22.3 | 3.99 | m |
| 23.2 | 3.83 | m |
| 24.0 | 3.71 | s |
| 25.3 | 3.52 | s |
| 26.3 | 3.38 | w |
| 27.6 | 3.23 | m |
| 29.0 | 3.08 | w |
| 29.9 | 2.99 | w |
| 31.4 | 2.85 | vw |
| 32.7 | 2.74 | w |

TABLE 6

D-Spacing Table for Form G (Methanol Solvate)

| Pos. [°2Th.] | d-value [Å] | Rel. Int. |
|---|---|---|
| 8.1 | 10.9 | vw |
| 8.5 | 10.3 | vw |
| 9.7 | 9.1 | vs |
| 10.7 | 8.2 | vw |
| 11.2 | 7.9 | m |
| 13.6 | 6.5 | w |
| 14.0 | 6.3 | s |
| 15.6 | 5.66 | vw |
| 16.1 | 5.49 | m |
| 16.5 | 5.38 | m |
| 17.2 | 5.16 | m |
| 17.7 | 5.01 | vw |
| 18.8 | 4.72 | s |
| 19.5 | 4.56 | m |
| 20.3 | 4.38 | m |
| 20.8 | 4.27 | m |
| 21.6 | 4.12 | m |
| 22.1 | 4.03 | m |
| 23.1 | 3.86 | s |
| 23.3 | 3.82 | vs |
| 24.5 | 3.63 | s |
| 25.7 | 3.46 | m |
| 27.3 | 3.27 | m |
| 28.5 | 3.13 | w |
| 29.4 | 3.04 | m |
| 30.9 | 2.89 | w |
| 33.1 | 2.70 | w |
| 34.0 | 2.64 | vw |

TABLE 7

D-Spacing Table for Form H (Isopropanol Solvate)

| Pos. [°2Th.] | d-value [Å] | Rel. Int. |
|---|---|---|
| 8.3 | 10.6 | vw |
| 9.7 | 9.1 | s |
| 10.8 | 8.2 | m |
| 11.0 | 8.1 | w |
| 13.4 | 6.6 | w |
| 13.9 | 6.4 | s |
| 15.7 | 5.65 | vw |
| 16.1 | 5.49 | m |
| 16.4 | 5.41 | m |
| 16.7 | 5.32 | s |
| 18.4 | 4.82 | m |
| 18.6 | 4.77 | m |
| 19.4 | 4.57 | m |
| 20.2 | 4.41 | s |
| 20.8 | 4.27 | m |
| 21.2 | 4.20 | s |
| 21.6 | 4.11 | m |
| 21.9 | 4.06 | m |
| 22.1 | 4.02 | m |
| 22.8 | 3.90 | s |
| 23.2 | 3.84 | w |
| 23.9 | 3.72 | vs |
| 24.3 | 3.66 | m |
| 25.1 | 3.55 | m |
| 25.5 | 3.50 | s |
| 26.0 | 3.43 | m |
| 26.9 | 3.31 | m |
| 27.6 | 3.23 | w |
| 28.3 | 3.16 | m |
| 29.3 | 3.05 | w |
| 29.7 | 3.01 | w |
| 30.5 | 2.93 | m |
| 31.7 | 2.83 | w |
| 32.0 | 2.80 | m |
| 32.7 | 2.74 | m |

TABLE 7-continued

D-Spacing Table for Form H (Isopropanol Solvate)

| Pos. [°2Th.] | d-value [Å] | Rel. Int. |
|---|---|---|
| 34.0 | 2.64 | vw |
| 34.8 | 2.58 | w |

TABLE 8

D-Spacing Table for Form I (Dichloromethane Solvate)

| Pos. [°2Th.] | d-value [Å] | Rel. Int. |
|---|---|---|
| 8.0 | 11.0 | vw |
| 8.7 | 10.2 | vw |
| 9.8 | 9.1 | vs |
| 10.7 | 8.3 | vw |
| 11.3 | 7.9 | m |
| 13.7 | 6.5 | w |
| 14.2 | 6.2 | s |
| 15.7 | 5.66 | w |
| 16.1 | 5.51 | m |
| 16.7 | 5.32 | m |
| 17.4 | 5.10 | m |
| 18.4 | 4.83 | vw |
| 18.9 | 4.69 | s |
| 19.6 | 4.54 | m |
| 20.4 | 4.36 | w |
| 20.9 | 4.24 | m |
| 21.5 | 4.14 | m |
| 22.2 | 4.01 | m |
| 23.3 | 3.82 | s |
| 24.2 | 3.68 | w |
| 24.8 | 3.59 | vs |
| 26.0 | 3.42 | s |
| 27.5 | 3.25 | s |
| 28.5 | 3.14 | w |
| 29.5 | 3.03 | m |
| 31.0 | 2.89 | vw |
| 32.7 | 2.74 | vw |
| 33.6 | 2.67 | w |
| 34.3 | 2.62 | vw |

TABLE 9

D-Spacing Table for Form J (2-butanone Solvate)

| Pos. [°2Th.] | d-value [Å] | Rel. Int. |
|---|---|---|
| 6.9 | 12.8 | w |
| 9.4 | 9.4 | vs |
| 11.3 | 7.8 | m |
| 11.7 | 7.6 | w |
| 12.4 | 7.1 | vw |
| 13.0 | 6.8 | vw |
| 14.1 | 6.3 | s |
| 15.7 | 5.64 | w |
| 16.3 | 5.45 | w |
| 17.3 | 5.13 | m |
| 17.7 | 5.00 | s |
| 18.4 | 4.82 | m |
| 18.9 | 4.69 | m |
| 19.3 | 4.60 | w |
| 19.8 | 4.49 | m |
| 20.0 | 4.45 | m |
| 21.0 | 4.23 | s |
| 21.5 | 4.14 | m |
| 22.0 | 4.04 | w |
| 22.5 | 3.96 | m |
| 22.9 | 3.88 | vs |
| 23.6 | 3.77 | w |
| 24.1 | 3.69 | vw |
| 24.9 | 3.57 | vs |
| 26.2 | 3.41 | m |

TABLE 9-continued

D-Spacing Table for Form J (2-butanone Solvate)

| Pos. [°2Th.] | d-value [Å] | Rel. Int. |
|---|---|---|
| 27.1 | 3.29 | w |
| 27.6 | 3.23 | vw |
| 28.3 | 3.16 | m |
| 28.5 | 3.13 | m |
| 30.0 | 2.98 | w |
| 30.3 | 2.95 | w |
| 30.8 | 2.90 | vw |
| 32.1 | 2.79 | vw |
| 32.7 | 2.74 | w |
| 33.4 | 2.68 | m |
| 34.4 | 2.61 | vw |
| 34.9 | 2.57 | vw |

What is claimed is:

1. A crystalline form of 5-methyl-pyridine-2-sulfonic acid [6-methoxy-5-(2-methoxy-phenoxy)-2-pyridin-4-yl-pyrimidin-4-yl]-amide which exhibits a characteristic X-ray powder diffraction pattern with characteristic peaks expressed in d-values (Å), measured with a conventional powder X-ray diffractometer using $Cu_{K\alpha}$ radiation: 9.0 (vs), 7.8 (m), 6.2 (s), 5.48 (m), 5.30 (m), 5.07 (m), 4.67 (s), 4.52 (m), 4.23 (m), 4.14 (m) 3.79 (m), 3.57 (s), 3.42 (m), 3.23(m) and 3.02(m); designated as form A.

2. A crystalline form of 5-methyl-pyridine-2-sulfonic acid [6-methoxy-5-(2-methoxy-phenoxy)-2-pyridin-4-yl-pyrimidin-4-yl]-amide which exhibits a characteristic X-ray powder diffraction pattern with characteristic peaks expressed in d-values (Å), measured with a conventional powder X-ray diffractometer using $Cu_{K\alpha}$ radiation: 10.7 (m), 9.4 (m), 8.6 (vs), 8.3 (m), 7.6 (m), 6.7 (m), 6.4 (m), 6.0 (m), 5.69 (m), 5.30 (m), 5.17 (m), 4.95 (vs), 4.76 (m), 4.56 (m), 4.43 (s), 4.13 (vs), 3.80 (s), 3.45 (s), 3.41 (s), 3.37 (s) and 3.03 (m); designated as form B.

3. A crystalline pseudo-polymorph of 5-methyl-pyridine-2-sulfonic acid [6-methoxy-5-(2-methoxy-phenoxy)-2-pyridin-4-yl-pyrimidin-4-yl]-amide selected from the group consisting of:

a) the pseudo-polymorph, ethanol solvate, which exhibits a characteristic X-ray powder diffraction pattern with characteristic peaks expressed in d-values (Å), measured with a conventional powder X-ray diffractometer using $Cu_{K\alpha}$ radiation: 9.0 (vs), 8.1 (m), 6.4 (s), 5.46 (m), 5.29 (s), 4.77 (m), 4.55 (m), 4.38 (s), 4.26 (m), 4.14 (m), 4.08 (m), 4.02 (m), 3.87 (s), 3.70 (vs), 3.48 (vs), 3.28 (m), 3.13 (m) and 3.04 (m); designated as form D;

b) the pseudo-polymorph, acetone hemi solvate, which exhibits a characteristic X-ray powder diffraction pattern with characteristic peaks expressed in d-values (Å), measured with a conventional powder X-ray diffractometer using $Cu_{K\alpha}$ radiation: 13.0 (w), 9.1 (vs), 7.9 (m), 6.2 (m), 5.61 (m), 5.51 (w), 5.06 (m), 4.75 (m), 4.57 (m), 4.40 (m), 4.34 (m), 4.17 (m), 3.88 (s), 3.56 (s), 3.32 (m) and 3.05 (m); designated as form E;

c) the pseudo-polymorph, tetrahydrofuran solvate, which exhibits a characteristic X-ray powder diffraction pattern with characteristic peaks expressed in d-values (Å), measured with a conventional powder X-ray diffractometer using $Cu_{K\alpha}$ radiation: 9.2 (vs), 8.3 (m), 7.8 (m), 6.4 (m), 6.3 (m), 5.75 (m), 5.27 (m), 4.89 (m), 4.62 (m), 4.53 (m), 4.39 (m), 4.22 (m), 4.06 (m), 3.99 (m), 3.83 (m), 3.71 (s), 3.52 (s) and 3.23 (m); designated as form F;

d) the pseudo-polymorph, methanol solvate, which exhibits a characteristic X-ray powder diffraction pattern with characteristic peaks expressed in d-values (Å), measured with a conventional powder X-ray diffractometer using $Cu_{K\alpha}$ radiation: 9.1 (vs), 7.9 (m), 6.3 (s), 5.49 (m), 5.38 (m), 5.16 (m), 4.72 (s), 4.56 (m), 4.38 (m), 4.27 (m), 4.12 (m), 4.03 (m), 3.86 (s), 3.82 (vs), 3.63 (s), 3.46 (m) and 3.27 (m); designated as form G;

e) the pseudo-polymorph, isopropanol solvate, which exhibits a characteristic X-ray powder diffraction pattern with characteristic peaks expressed in d-values (Å), measured with a conventional powder X-ray diffractometer using $Cu_{K\alpha}$ radiation: 9.1 (s), 8.2 (m), 6.4 (s), 5.32 (s), 4.82 (m), 4.77 (m), 4.57 (m), 4.41 (s), 4.27 (m), 4.20 (s), 4.11 (m), 4.06 (m), 4.02 (m), 3.90 (s), 3.72 (vs), 3.50 (s), 3.43 (m), 3.16 (m) and 2.74 (m); designated as form H;

f) the pseudo-polymorph, dichloromethane solvate, which exhibits a characteristic X-ray powder diffraction pattern with characteristic peaks expressed in d-values (Å), measured with a conventional powder X-ray diffractometer using $Cu_{K\alpha}$ radiation: 9.1 (vs), 7.9 (m), 6.2 (s), 5.51 (m), 5.32 (m), 5.10 (m), 4.69 (s), 4.54 (m), 4.24 (m), 4.14 (m), 4.01 (m), 3.82 (s), 3.59 (vs), 3.42 (s), 3.25 (s) and 3.03 (m); designated as form I; and g) the pseudo-polymorph, 2-butanone, which exhibits a characteristic X-ray powder diffraction pattern with characteristic peaks expressed in d-values (Å), measured with a conventional powder X-ray diffractometer using $Cu_{K\alpha}$ radiation: 9.4 (vs), 7.8 (m), 6.3 (s), 5.13 (m), 5.00 (s), 4.82 (m), 4.69 (m), 4.49 (m), 4.45 (m), 4.23 (s), 4.14 (m), 3.96 (m), 3.88 (vs), 3.57 (vs), 3.41 (m), 3.16 (m), 3.13 (m) and 2.68 (m); designated as form J.

4. A process for the preparation of crystal form A of 5-methyl-pyridine-2-sulfonic acid [6-methoxy-5-(2-methoxy-phenoxy)-2-pyridin-4-yl-pyrimidin-4-yl]-amide, according to claim 1, comprising dissolving a salt of 5-methyl-pyridine-2-sulfonic acid [6-methoxy-5-(2-methoxy-phenoxy)-2-pyridin-4-yl-pyrimidin-4-yl]-amide in water or water containing a cosolvent, precipitating the free base by adding an acid, isolating and drying the solid residue.

5. A process for the preparation of crystal form B of 5-methyl-pyridine-2-sulfonic acid [6-methoxy-5-(2-methoxy-phenoxy)-2-pyridin-4-yl-pyrimidin-4-yl]-amide, according to claim 2, comprising suspending or dissolving a solid form other than form B of 5-methyl-pyridine-2-sulfonic acid [6-methoxy-5-(2-methoxy-phenoxy)-2-pyridin-4-yl-pyrimidin-4-yl]-amide at a temperature from 20° C. to 100° C. in a solvent, optionally cooling the solution to precipitate 5-methyl-pyridine-2-sulfonic acid [6-methoxy-5-(2-methoxy-phenoxy)-2-pyridin-4-yl-pyrimidin-4-yl]-amide, stirring the suspension for a time sufficient to complete formation of crystal form B, removing the solvent and drying the solid residue.

6. A process according to claim 5, wherein the solvent used is essentially free of water.

7. A process according to claim 6, wherein the solvent is selected from the group comprising methyl tert.-butyl ether, acetone, acetonitrile, hexane and mixtures thereof.

8. A process for the preparation of crystal form B of 5-methyl-pyridine-2-sulfonic acid [6-methoxy-5-(2-methoxy-phenoxy)-2-pyridin-4-yl-pyrimidin-4-yl]-amide, according to claim 2, comprising heating form A or a mixture of forms A and B of 5-methyl-pyridine-2-sulfonic acid [6-methoxy-5-(2-methoxy-phenoxy)-2-pyridin-4-yl-pyrimidin-4-yl]-amide, preferably under a protective atmosphere, to a temperature of 80° C. to 160° C. with optional mixing for a time sufficient to form crystal form B.

9. A pharmaceutical composition comprising crystal form A, according to claim 1, form B, according to claim 2, or form D to J, according to claim 3, of 5-methyl-pyridine-2-sulfonic acid [6-methoxy-5-(2-methoxy-phenoxy)-2-pyridin-4-yl-pyrimidin-4-yl]-amide and a pharmaceutically acceptable carrier or diluent.

* * * * *